United States Patent [19]

Curtis

[11] Patent Number: 5,064,282

[45] Date of Patent: Nov. 12, 1991

[54] PHOTOMETRIC APPARATUS AND METHOD FOR MEASURING HEMOGLOBIN

[75] Inventor: Richard H. Curtis, Gorham, Me.

[73] Assignee: Artel, Inc., South Windham, Mass.

[21] Appl. No.: 412,899

[22] Filed: Sep. 26, 1989

[51] Int. Cl.$^5$ .................... G01N 33/49; G01N 21/03
[52] U.S. Cl. ..................................... 356/40; 356/246
[58] Field of Search ..................... 356/39, 40, 41, 246

[56] References Cited

U.S. PATENT DOCUMENTS

| | | | |
|---|---|---|---|
| 3,492,095 | 1/1970 | Tillem | 23/230 |
| 3,565,537 | 2/1971 | Fielding | 356/246 |
| 3,705,000 | 12/1972 | Guerra | 356/246 |
| 4,248,536 | 2/1981 | Hijikata | 356/416 |
| 4,305,659 | 12/1981 | Bilstad et al. | 356/40 |
| 4,357,105 | 11/1982 | Liretz | 356/40 |
| 4,405,235 | 9/1983 | Rossiter | 356/246 |
| 4,582,684 | 4/1986 | Vogel et al. | 422/57 |
| 4,595,561 | 6/1986 | Thornton et al. | 422/58 |

OTHER PUBLICATIONS

Von Schneck et al., "Evaluation of HemoCue, A New Device For Determining Hemoglobin", Clinical Chemistry, vol. 32, No. 3 (Mar. 1986).

Primary Examiner—Vincent P. McGraw
Attorney, Agent, or Firm—Wolf, Greenfield & Sacks

[57] ABSTRACT

An apparatus and method for making a photometric absorbance measurement of hemoglobin in a blood sample utilizing a reusable cuvette and an inexpensive photometer. The cuvette is a unitary plastic body having a flow-through slot of a predetermined height which allows an absorbance measurement to be made with an undiluted blood sample and which permits cleaning by inserting the body in a liquid cleaning solution. Two absorbance measurements are made, the first at a wavelength at which the absorbance of oxyhemoglobin and deoxyhemoglobin are approximately equal, near an isobestic point, and a second measurement at which these components absorb substantially no light. By making the first measurement near an absorbance minimum at about 510 nm, an absorbance measurement can be made with a relatively thick slot required for cleaning and with an undiluted blood sample and an inexpensive photometer.

24 Claims, 3 Drawing Sheets

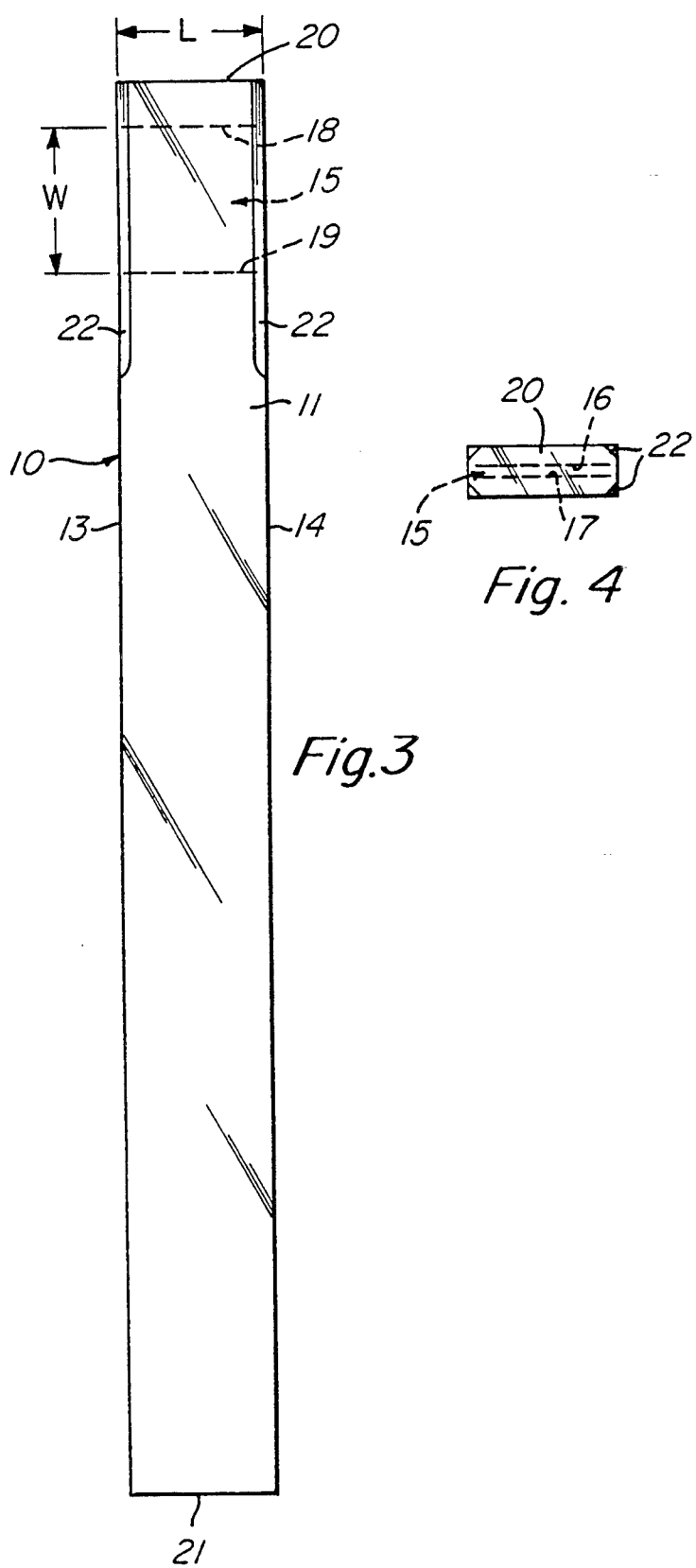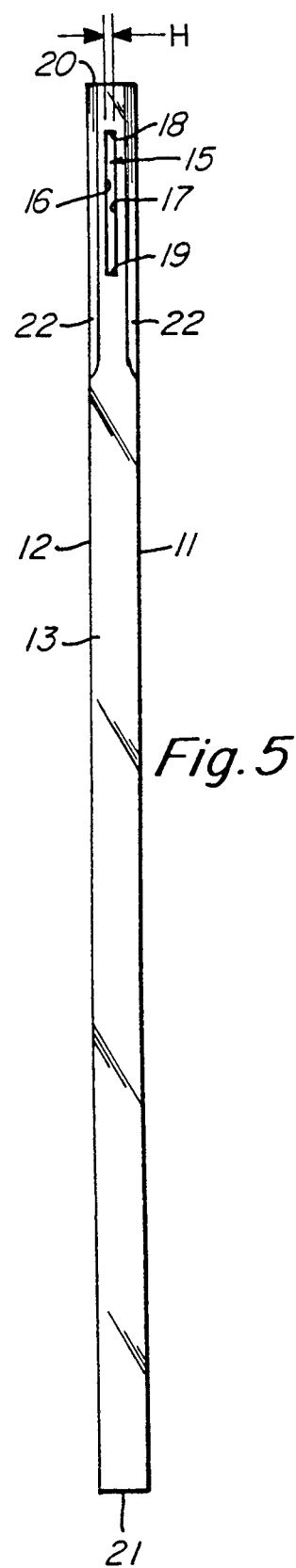

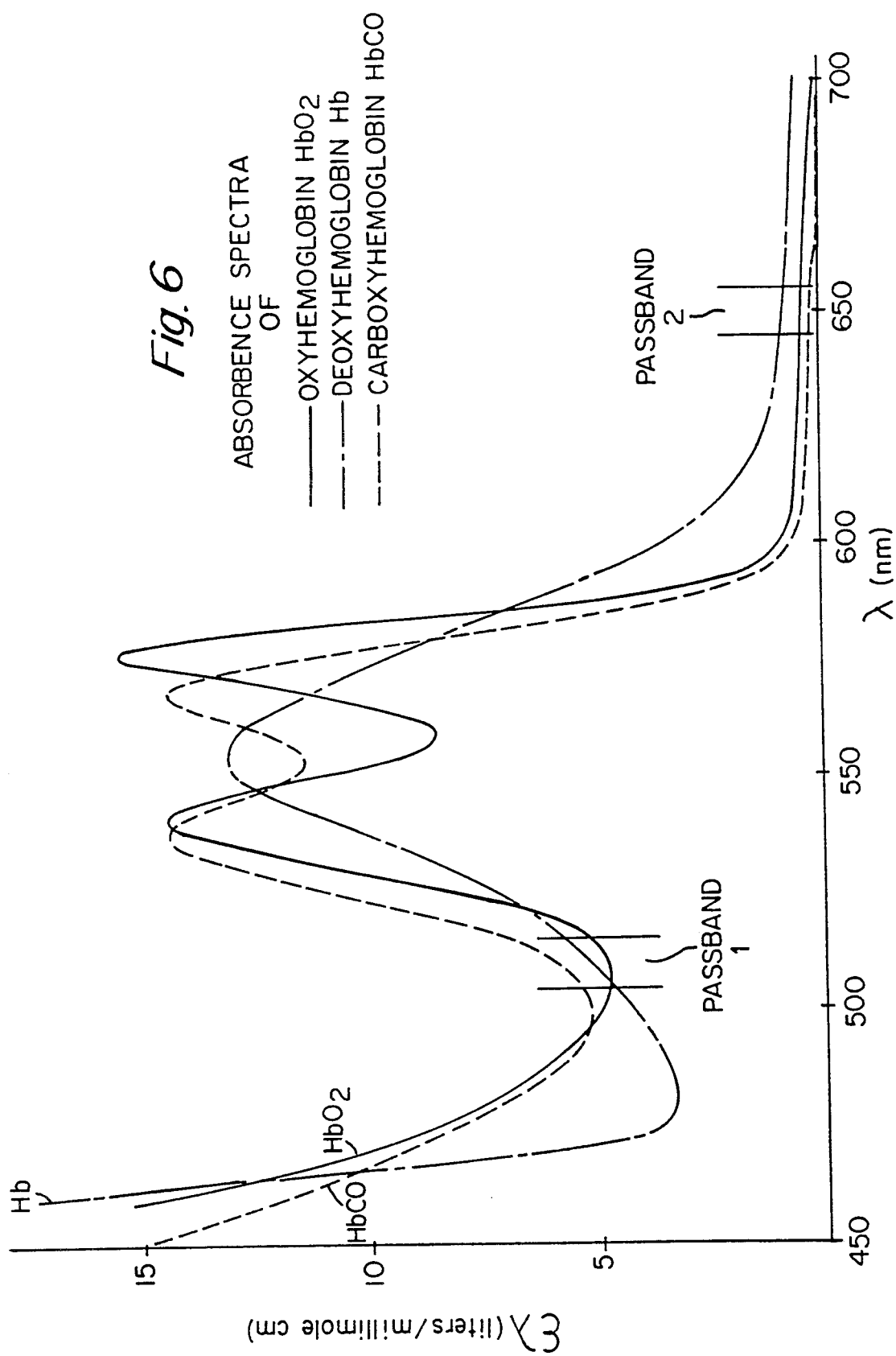

PHOTOMETRIC APPARATUS AND METHOD FOR MEASURING HEMOGLOBIN

BACKGROUND OF THE INVENTION

This invention concerns a photometric method of making an absorbance measurement at selected wavelengths with a specially designed cuvette, and more specifically to a method and apparatus which enables accurate measurements of hemoglobin to be made in the field with a relatively inexpensive photometer and a reusable cuvette.

Where large numbers of hemoglobin measurements are made in the field, such as in third-world countries, it is desirable to avoid any system which requires the use of reagents (which increase the cost and require proper storage), high dilution of the blood sample (which leads to inaccuracies), or disposable cuvettes (which increase the cost and generate waste). Also, it is desirable to use a system which enables an accurate measurement to be made with a relatively inexpensive photometer. The method and apparatus of this invention meets these requirements and thus allows accurate measurements of hemoglobin to be made in the field on a large scale at a relatively low cost.

SUMMARY OF THE INVENTION

The cuvette of this invention is a unitary body of a rigid, optically transparent material, such as clear plastic. The cuvette body is in the shape of a slide having opposing upper and lower planar faces and opposing first and second side edges. A flow through slot is disposed between the upper and lower planar faces and extends between the first and second side edges. The dimensions of the slot are selected such that a blood sample can be drawn into the slot by capillary action, and yet the slot is large enough to allow a solution of water and detergent to flow through and clean the slot so that the cuvette is reusable. Still further, the dimensions of the slot enable a hemoglobin absorbance measurement to be made at selected wavelengths on an undiluted blood sample in the slot.

According to the method of the invention, the selected wavelengths include a first passband centered at about 510 nm, the wavelength at which the two major forms of hemoglobin: oxyhemoglobin and deoxyhemoglobin, absorb about equally, and a second passband centered at about 650 nm, at which substantially no absorbance occurs. Utilizing a wavelength at which oxyhemoglobin and deoxyhemoglobin absorb almost equally (the "isobestic point), insures an accurate absorbance measurement regardless of the proportion of these two components. A third major hemoglobin component in smokers is carboxyhemoglobin, which has an absorbance differing only slightly from the other two at 510 nm and has been shown to have a minimal impact on the accuracy of this method. Furthermore, utilizing the isobestic point, which is near an absorbance minimum, allows a hemoglobin measurement to be taken with an undiluted blood sample in the reusable cuvette of this invention and with an inexpensive photometer. Finally, by taking the difference between the absorbance measurements at the two passbands, an accurate determination of absorbance is obtained which compensates for any dirt on the cuvette, turbidity of the sample, changes in the light source, scratches on the cuvette, or other system variables which affect the absorbance output.

The use of high-cost reagents are avoided in this method. The only reagent required is a lysing agent which breaks up the erythrocytes to release the hemoglobin. The use of an undiluted sample avoids inaccuracies which occur when blood is sampled into a capillary device and is diluted by untrained people at outpatient units rather than by laboratory technicians. Furthermore, because the cuvettes are reusable, the cost thereof is reduced and the waste generated by the procedure is substantially reduced. Still further, a relatively inexpensive photometer can be used by taking an absorbance measurement at less than the maximum absorbance.

BRIEF DESCRIPTION OF THE DRAWINGS

FIG. 3 is a top plan view of the cuvette of this invention.

FIG. 4 is an end plan view of the cuvette of FIG. 3.

FIG. 5 is a side plan view of the cuvette of FIG. 3.

FIG. 6 is a graph of the absorbance spectra of three different forms of hemoglobin showing the selected passbands used in this invention.

DETAILED DESCRIPTION OF THE PREFERRED EMBODIMENT

Figure 1:
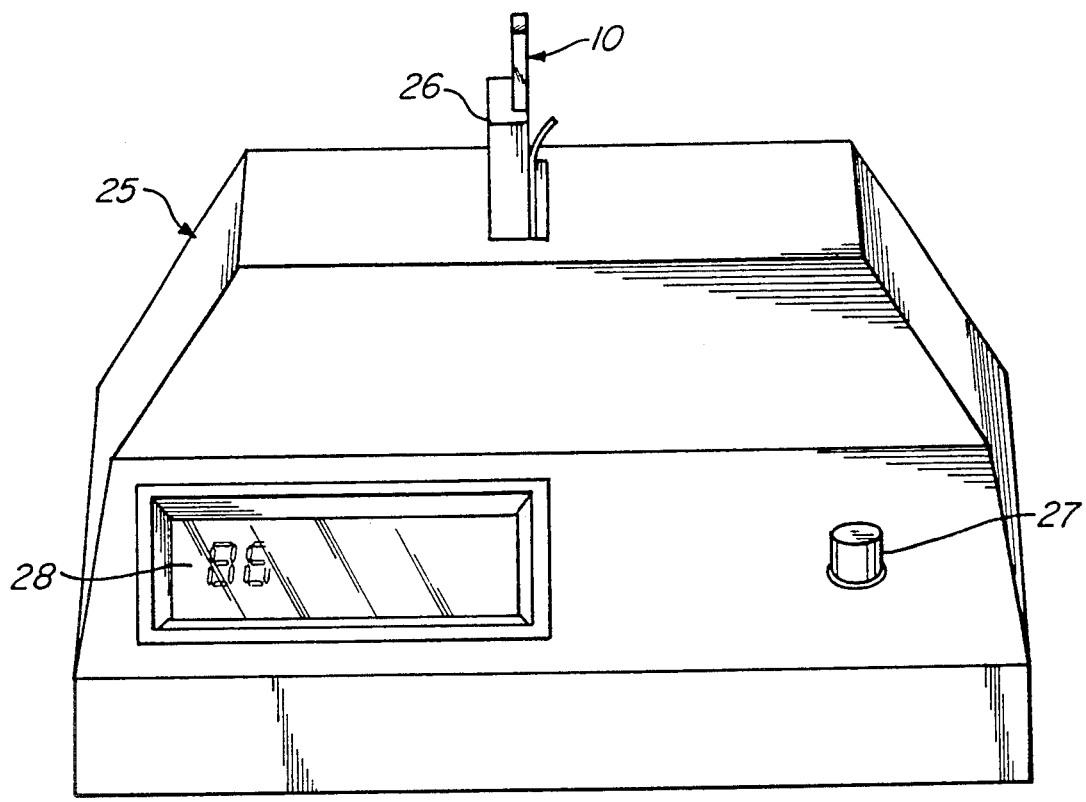
FIG. 1 is a perspective view of a photometric instrument for measuring hemoglobin.

Described herein is a preferred embodiment of the apparatus and method of this invention for making an absorbance measurement of hemoglobin in an undiluted blood sample. The invention, however, is not limited to this application and may be used for making a photometric determination of a component of any liquid sample, provided that several stipulations are satisfied: (1) there are no interfering substances present in the sample which absorb sufficiently at the chosen passbands to degrade the accuracy of the measurement; and (2) if the sample does consist of a mixture of substances, that either the proportions of each are well known or the absorbances of the substances are equal at the chosen passbands.

As shown in FIG. 6, the absorbance of each of the three forms of hemoglobin—oxyhemoglobin ($HbO_2$), deoxyhemoglobin (Hb), and carboxyhemoglobin HbCO), vary with wavelength. Selected absorbance characteristics of these hemoglobin components are used in combination with selected dimensions of the sample slot in the cuvette in order to allow an accurate absorbance measurement to be made with an undiluted sample, an inexpensive photometer, and a reusable flow-through cuvette.

As shown in FIGS. 3-5, the cuvette 10 is a unitary body of molded plastic in the shape of a flat, rectangular slide. The cuvette has flat, parallel upper and lower faces 11, 12, opposing side edges or walls 13, 14 perpendicular to the upper and lower faces and disposed along the long edges of the rectangular faces, and opposing end walls 20, 21 perpendicular to and disposed between the short edges of the faces. In this preferred embodiment, the upper and lower faces 11, 12 are 2.00" long and 0.200" wide. The side edges 13, 14 and end walls 20, 21 are each 0.060" in height.

Disposed between upper and lower faces 11, 12 and extending between opposing side edges 13, 14 is a slot 15 of width W, length L, and height H. In the preferred embodiment shown, W=0.200", L=0.200", and H=0.0100". The upper and lower walls 16, 17 of slot 15 are parallel to cuvette faces 11 and 12 and the slot sidewalls 18, 19 are parallel to the opposing end walls 20, 21 of the cuvette. The length L of the slot is disposed perpendicular to the long side edges of cuvette faces 11, 12. Beveled edges 22 are provided along the side edges 13, 14 of the cuvette adjacent the slot to facilitate the capillary flow of blood into the slot. The cuvette is injection molded as a unitary body, with no separate parts, preferably of LEXAN polycarbonate sold by General Electric, Polymers product Dept., Pittsfield, Mass.

The slot dimentions are specifically defined in accordance with this invention. It has been found that a slot thickness H of 0.003" cannot be readily cleaned of blood constituents, whereas a slot 0.010" thick can be cleaned easily in a detergent solution.

A second reason to have a relatively thick slot is to minimize the effect of manufacturing tolerance on instrument performance. For a given tolerance in slot thickness, a thicker slot will result in a lower percentage error in the light path through the sample, and therefore better overall instrument accuracy and precision.

The requirement that the slot in the cuvette have an accurately known and maintained thickness, in order to guarantee instrument accuracy, precludes the use of a cuvette which can be opened or disassembled for cleaning. It has been found that any cuvette which can be opened and reclosed is sensitive to any small piece of dust or grit in the closure mechanism. If the mechanism is manufactured with a very small clearance so that the cuvette recloses to equal thickness each time, then a small amount of contamination will jam the mechanism and prevent closure. If more generous clearances are provided, then the same grit or contamination will cause the cuvette to reclose with a different slot thickness each time, causing poor accuracy in the results. In this embodiment, the slot height H is preferably of from about 0.0095" to about 0.0105" (a 5% tolerance) and more preferably of from about 0.0098" to about 0.0102" (a 2% tolerance).

Figure 2:
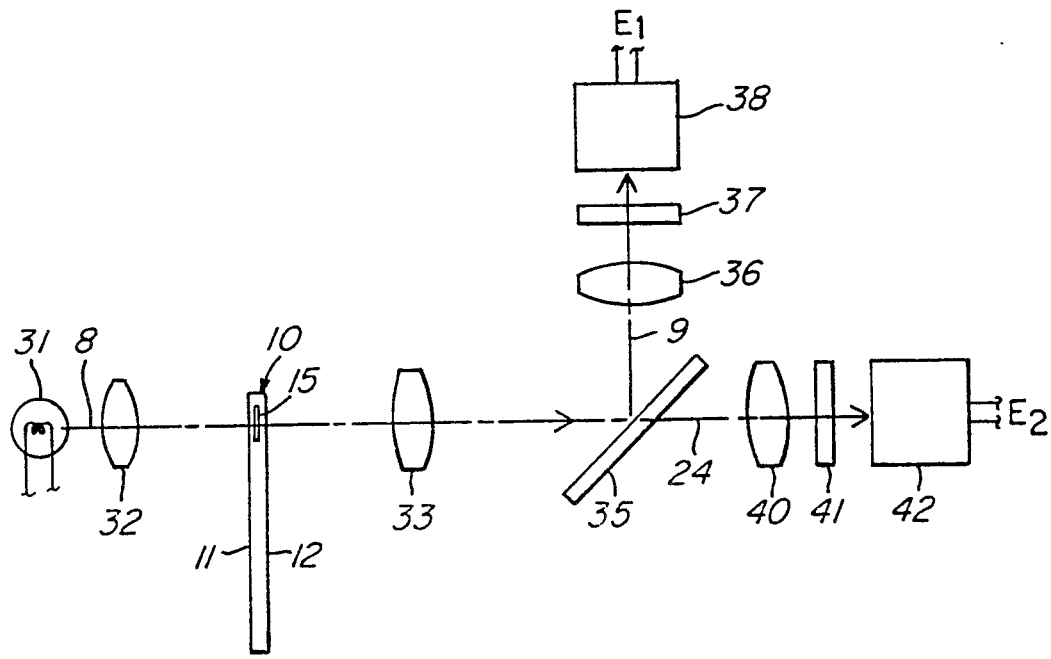
FIG. 2 is a schematic diagram of the optical system of the photometer of FIG. 1.

The photometer 25 shown in FIGS. 1-2 includes a removable holder 26 in which the cuvette 10 is placed and inserted in the top of the instrument. The instrument has an "ON" button 27 and digital display 28 on its front surface. The light path within the instrument, as shown in FIG. 2, includes an incandescent light source 31 at one end which emits a light beam 8. Disposed in serial relationship between light source 31 and beam splitter 35 are a collimating lens 32, cuvette 10, and a converging lens 33. Light beam 8 emitted from light source 31 is collected by lens 32, and exits as a collimated beam which passes through slot 15 in cuvette 10, and is collected by lens 33 and focused on beam splitter 35. Cuvette 10 is positioned so that its opposing faces 11, 12, and the upper and lower walls 16, 17 of the slot, are perpendicular to the beam 8. Beam 8 thus passes through the slot 15 parallel to its height H.

At beam splitter 35, 10% of beam 8 is reflected as light beam 9 to first collimating lens 36, first filter 37, and first photodetector 38, in serial relation. Lens 36 passes a collimated beam 9 through first filter 37 and the beam exiting filter 37 strikes photodetector 38, the output of which is an intensity measurement of beam 9.

Beam splitter 35 transmits the remaining 90% of beam 8 as beam 18 which passes serially through second collimating lens 40, second filter 41, and second photodetector 42 Lens 40 transmits a collimated beam through filter 41 and the beam exiting filter 41 strikes photodetector 42, the output of which is an intensity measurement of beam 18.

The passbands of filters 37 and 41 and the dimensions of slot 15, in particular the height H, are selected to allow a hemoglobin measurement to be made with an undiluted blood sample and with an inexpensive photometer at the selected wavelengths, while providing a slot of sufficiently large dimensions to permit flow through cleaning of the slot.

In the preferred embodiment, slot 15 holds a 6.5 microliter sample of undiluted blood wherein the slot has a height H=0.0100", a width W=0.200", a length L=0.200". The slot is sufficiently small to allow the blood sample to be drawn into the slot by capillary action. The slot is sufficiently large to allow effective cleaning of the slot by dipping the cuvette into a solution of water and detergent and swishing the cuvette in the solution.

The first passband is centered at 510 nm, at which oxyhemoglobin and deoxyhemoglobin absorb about equally. This wavelength is less than the maximum absorbance at 540 nm, and is selected to enable an accurate measurement to be made with an inexpensive photometer for an undiluted blood sample in the cuvette slot of designated height H. A second passband of 650 nm is selected at which substantially no absorbance by hemoglobin occurs. The amount of hemoglobin present in the sample is calculated from the following equation:

hemoglobin content in grams/liter = $C \log (E_2/E_1)$ where $E_1$ is the output of the first photodetector 38, $E_2$ is the output of the second photodetector 42, and C is a calibration constant determined by the system. The outputs $E_1$ and $E_2$ are processed by an electronic circuit and the resulting hemoglobin valve displayed on digital display 28.

As can be seen from FIG. 4, the average extinction values for oxy and deoxyhemoglobin are not quite the same either in the range of passband 1 or passband 2. It is of course the difference in extinction coefficients between the two passbands which the instrument measures. These differences are:

For Hb: $\Delta\epsilon_\lambda = 5.25 - 0.75 = 4.50$
For HbO$_2$: $\Delta\epsilon_\lambda = 4.80 - 0.35 = 4.45$
For HbCO: $\Delta\epsilon_\lambda = 5.80 - 0.20 = 5.60$ Passband 1 has been chosen to be centered at 510 nm in order to make $\Delta\epsilon_\lambda$ nearly the same for oxy and deoxyhemoglobin.

In practice, the hemoglobin in blood is between 75 and 100% oxygenated, depending on the source of the sample and the manner in which it has been handled after drawing. See Norbert Tietz, Textbook of Clinical Chemistry, W. B. Saunders Co., Philadelphia, p. 1555 (1986). The maximum error in total hemoglobin measurement due to variations in oxygenation is 0.3% when the passbands are centered at 510 and 650 nm.

Another potential source of error is the presence of carboxyhemoglobin in the blood. In heavy smokers it can be up to 10% of the total hemoglobin. The presence of carboxyhemoglobin may elevate the hemoglobin reading by up to 2% over a true total hemoglobin reading. Field trials were conducted to test the sensitivity of this method to the presence of carboxyhemoglobin; substantially no sensitivity was found.

The absorbance of blood containing 20 g/dl of hemoglobin (the upper limit of the human range) when measured undiluted in a 0.010" thick cuvette at 510 nm is 1.90 OD (optical density). If the measurement were made at 540 nm, the absorbance peak, the absorbance would be 5.7 OD. The latter is too high an absorbance to be measured except by the most expensive and sophisticated spectrophotometers, e.g., Varian Cary model 220. As an alternative, the cuvette could be made thinner, say 0.003" thick. This would give low absorbance values (below 2.0 OD) even if the measurement were made at 540 nm, however the cuvette would need to be taken apart to be cleaned, which introduces accuracy problems as previously discussed. The inexpensive photometer used herein includes as a light source a tungsten filament lamp L1021, sold by Gilway Technical Lamps, Woburn, Mass., and as photodetectors two S2386-5K detectors sold by Hamamatsu, Bridgewater, N.J. The resolution of the instrument is 0.1 g/dl of hemoglobin. The accuracy, as determined in a clinical trial comparing this instrument to a Coulter s-plus STKR (Coulter Electronics, Hialeah, Fla.), was 0.4 g/dl, or 3% (standard error of the estimate for 81 samples).

The cuvette and instrument are designed to be used in the field, and more particularly in third-world countries where it is desirable to avoid any system which requires the use of expensive reagents, high dilution of the sample, or disposable cuvettes. Also, the cuvette enables an accurate measurement to be made with a relatively inexpensive photometer. The cuvette is an injection molded, one-piece body of plastic in the shape of a slide, with a flow-through slot. It is inexpensive to produce and because it is reusable, it reduces the waste generated by the system. Furthermore, because there are no movable or separate parts involving the slot in the cuvette, it is not possible for the slot's dimensions to change which would affect the absorbance measurement. Still further, the slot is easily cleaned by inserting the cuvette in a solution of water and detergent and swishing the cuvette in the solution so that water flows through the slot.

Still further, by using an undiluted sample, the errors inherent in diluting the sample are avoided. Furthermore, the only reagent required is saponin, a natural substance which acts as a lysing agent and breaks up the erythrocytes to release hemoglobin. In use, a drop of blood is placed on a glass slide, a stick having saponin thereon is stirred with the blood until translucent, and the cuvette slot is placed against the blood on the slide whereby the blood is drawn into the slot by capillary action. To clean the slot and sterilize the cuvette, a solution of detergent and water to which a small amount of chlorine bleach (5-10%) has been added may be used.

The invention is not limited to the dimensions of the specific cuvette defined herein. More broadly, the slot may have a height defined between the opposing upper and lower faces of from about 0.005" to about 0.025", which will allow drawing of the sample into the slot by capillary action, and cleaning of the slot by swishing in a liquid cleaning solution. A preferred range of slot height is from about 0.005" to about 0.015" when making an absorbance measurement on a blood sample. The slot preferably holds a blood sample of from about 1 to about 20 microliters. The slot preferably has a length extending between the opposing first and second side edges of from about 0.1" to 0.3" and a width parallel to the side edges of from about 0.1" to about 0.3".

The first passband is preferably less than about 50% of the maximum absorbance characteristic of the component to be measured and the second passband is preferably at least about 5% of the maximum absorbance characteristic. For measuring hemoglobin, the first passband is preferably at about 500 to about 520 nm and the second passband at about 600 to 900 nm.

When the light source is an incandescent lamp, the passbands may be defined by interference or color glass filters. Alternatively, the light source may be one or several LEDs, in which case the passbands may be defined solely by the emission spectra of the LEDs or may be further defined by the addition of interference filters.

For example, a blue light emitting diode (LED) may be substituted for the incandescent lamp. A suitable diode is SLB5410 sold by Siemens Components Inc., Iselin, N.J. This diode principally emits in the region 450 to 540 nm, but has enough intensity at 650 nm to be useful in the preferred method described herein. The optical configuration would be the same as FIG. 2, with passband filters again in the ranges of 510 and 650 nm.

Another alternative is to use two LEDs, one principally emitting in the blue region and one in the red. These two LEDs may be mounted closely together in one package so they would act as one source and then turned on alternately. The alternating beams of red (approximately 650 nm) and blue (approximately 450 to 520 nm) light would pass through the sample and into a single detector. There would be no beam splitter. The two signals from the one detector would then be processed sequentially and the mathematical analysis performed as previously described.

Although a preferred embodiment of the invention has hereinbefore been described, it will be appreciated that variations of the invention will be perceived by those skilled in the art, which variations are nevertheless within the scope of the invention as defined by the claims appended hereto.

What is claimed is:

1. A cuvette for making a photometric measurement of a liquid sample comprising:

a unitary body of a rigid, solid material having opposing upper and lower faces and opposing first and second side edges;

a flow through slot disposed between the upper and lower faces and extending between the first and second side edges;

the slot being of a predetermined size such that a liquid sample may be drawn into the slot by capillary action and wherein a liquid cleaning solution will flow through and clean the slot when the body is inserted into and moved through the solution; and the body being optically transparent to allow photometric measurements to be made of a liquid sample in the slot.

2. The cuvette of claim 1, wherein the slot has a height defined between the opposing upper and lower faces of from about 0.005 to about 0.025 inches.

3. The cuvette of claim 2, wherein the slot has a length extending between the opposing first and second side edges of from about 0.1 to about 0.3 inches.

4. The cuvette of claim 3, wherein the slot has a width parallel to the side edges of from about 0.1 to about 0.3 inches.

5. The cuvette of claim 2, wherein the slot holds a sample of from about 1 to about 20 microliters.

6. The cuvette of claim 1, wherein the slot is of a predetermined size adapted for making an absorbance measurement with a blood sample.

7. The cuvette of claim 6, wherein the height of the slot is from about 0.005 to about 0.015 inches.

8. The cuvette of claim 7, wherein the height of the slot is about 0.01".

9. The cuvette of claim 1, wherein the body is in the shape of a slide.

10. The cuvette of claim 1, wherein the body is made of molded plastic.

11. Apparatus for making a photometric measurement wherein light passes through a liquid sample contained in a cuvette and a photometric detector measures the intensity of light passing through the sample, the improvement comprising:

a cuvette comprising a unitary body of a rigid, solid material having opposing upper and lower faces and opposing first and second side edges, a flow through slot disposed between the upper and lower faces and extending between the first and second side edges, the slot being of a predetermined size such that a liquid sample may be drawn into the slot by capillary action and a liquid cleaning solution will flow through and clean the slot when the body is inserted in and moved through the solution, the material being optically transparent to allow a photometric measurement to be made of a liquid sample in the slot;

means for measuring the intensity of light passing through the sample in the slot at a first passband wavelength less than the maximum absorbance characteristic of the sample;

wherein the predetermined size of the cuvette and the first passband are selected to allow both flow through cleaning of the slot and an absorbance measurement on an undiluted liquid sample.

12. The apparatus of claim 11 adapted for making an absorbance measurement with a blood sample, wherein the first passband is at about 500 to about 520 nm, and the slot has a height defined between the opposing faces of from about 0.005 to about 0.015 inches.

13. The apparatus of claim 12, wherein the first passband is centered at about 510 nm and the height of the slot is about 0.01 inches.

14. The apparatus of claim 11, further comprising:

means for measuring the intensity of light passing through the sample in the slot at a second passband wavelength at which substantially no absorbance occurs to enable an accurate absorbance measurement to be made by taking a ratio of the outputs from the first and second measuring means.

15. The apparatus of claim 14, wherein the first passband is at less than about 50% of the maximum absorbance characteristic and the second passband is at less than about 5% of the maximum absorbance characteristic.

16. The apparatus of claim 15, adapted for making a photometric absorbance measurement of hemoglobin wherein the first passband is at about 500 to about 520 nm and the second passband is at about 600 to about 900 nm.

17. The apparatus of claim 16, wherein the first passband is centered at about 510 nm and the second passband is centered at about 650 nm.

18. The apparatus of claim 17, wherein the slot has a height defined between the opposing faces of from about 0.005 to about 0.015 inches.

19. The apparatus of claim 14, further comprising:

an electronic circuit and a display device, the electronic circuit having measuring means for determining the ratio of the outputs of the two measuring means, means for determining the log of the ratio, means for multiplying the log of the ratio by a constant to produce a result, and means for sending the result to the display device.

20. A method of measuring the hemoglobin content of the blood comprising:

measuring the intensity of light passing through a blood sample at a first wavelength passband at which the absorbance of oxyhemoglobin and deoxyhemoglobin are approximately equal and are less than about fifty percent of their maximum absorbance;

measuring the intensity of light passing through a blood sample at a second passband wavelength at which both oxyhemoglobin and deoxyhemoglobin absorb substantially no light; and determining the ratio of the absorbances at the first and second wavelengths.

21. The method of claim 20, wherein the first passband is at about 500 to about 520 nm.

22. The method of claim 21, wherein the first passband is centered at about 510 nm.

23. The method of claim 21, wherein the second passband is at about 600 to about 900 nm.

24. The method of claim 21, wherein the intensity measurements are made with an undiluted blood sample of from about 0.005" to about 0.015" in thickness.

* * * * *